(12) United States Patent
Erhard et al.

(10) Patent No.: US 9,836,872 B2
(45) Date of Patent: Dec. 5, 2017

(54) METHODS FOR GENERATION OF EDGE=PRESERVING SYNTHETIC MAMMOGRAMS FROM TOMOSYNTHESIS DATA

(71) Applicant: KONINKLIJKE PHILIPS N.V., Eindhoven (NL)

(72) Inventors: Klaus Erhard, Hamburg (DE); Hanno Heyke Homann, Hannover (DE); Jonas Rikard Rehn, Sollentuna (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 121 days.

(21) Appl. No.: 14/896,811

(22) PCT Filed: Jun. 26, 2014

(86) PCT No.: PCT/EP2014/063463
§ 371 (c)(1),
(2) Date: Dec. 8, 2015

(87) PCT Pub. No.: WO2014/207080
PCT Pub. Date: Dec. 31, 2014

(65) Prior Publication Data
US 2016/0140749 A1    May 19, 2016

(30) Foreign Application Priority Data
Jun. 28, 2013   (EP) .................. 13174328

(51) Int. Cl.
*G06T 15/08*      (2011.01)
*G06T 15/20*      (2011.01)
(Continued)

(52) U.S. Cl.
CPC ............. *G06T 15/08* (2013.01); *A61B 6/025* (2013.01); *A61B 6/502* (2013.01); *G06T 15/205* (2013.01); *G06T 2210/41* (2013.01)

(58) Field of Classification Search
None
See application file for complete search history.

(56) References Cited

U.S. PATENT DOCUMENTS 5,218,534 A * 6/1993 Trousset ............... G06T 11/006
                                                        345/424
7,702,142 B2   4/2010  Ren et al.
(Continued)

FOREIGN PATENT DOCUMENTS

WO    WO 2015193296 A1 * 12/2015 ........... G06T 11/006

OTHER PUBLICATIONS

Arens, "A Survey of Transfer Functions Suitable for Volume Rendering", 8th IEEE/ EG Symposium on Volume Graphics, 2010, pp. 77-83; Eurographics Association ISBN: 978-3-905674-21-7.
(Continued)

*Primary Examiner* — Michael J Cobb

(57) ABSTRACT

A method and related apparatus (VS) for synthetic projection images, in particular synthetic 2D mammograms (S) formed from a 3D image volume T made up of slices (SL). It is proposed to compute a forward projection (FP) using a weighted average function that is implemented by a filter (FL). The filter function (FL) is configured such that that voxels in a slice with maximum sharpness are assigned highest weights thereby avoiding blurring by averaging with structurally less relevant slices.

20 Claims, 4 Drawing Sheets

(51) Int. Cl.
*A61B 6/00* (2006.01)
*A61B 6/02* (2006.01)

(56) References Cited

U.S. PATENT DOCUMENTS

| | | |
|---|---|---|
| 7,760,924 B2 | 7/2010 | Ruth et al. |
| 8,184,890 B2 | 5/2012 | Zhang et al. |
| 2005/0105679 A1* | 5/2005 | Wu .................. G06T 11/006 378/22 |
| 2005/0135559 A1* | 6/2005 | Hermann Claus .... G06T 11/005 378/91 |
| 2005/0152590 A1* | 7/2005 | Thieret ................ G06T 11/006 382/131 |
| 2007/0147674 A1* | 6/2007 | Gundel .................... G06T 5/20 382/131 |
| 2008/0025592 A1 | 1/2008 | Jerebko et al. |
| 2011/0150307 A1* | 6/2011 | Souza .................... G06T 5/002 382/131 |
| 2012/0308107 A1 | 12/2012 | Engel et al. |

OTHER PUBLICATIONS

"Hologic Introduces Synthesized 2D Image Algorithm Designed to Eliminate the Need for a 2D Mammogram in a 2D plus 3D Tomosynthesis Exam", Nov. 27, 2011.

B. Ren et al.: A new generation FFDM / tomosynthesis fusion system with selenium detector. Proc. SPIE 76220B-1, (2010).

* cited by examiner

US 9,836,872 B2

METHODS FOR GENERATION OF EDGE=PRESERVING SYNTHETIC MAMMOGRAMS FROM TOMOSYNTHESIS DATA

CROSS REFERENCE TO RELATED APPLICATIONS

This application is a national filing of PCT application Serial No. PCT/EP2014/063463, filed Jun. 26, 2014, published as WO 2014/207080 on Dec. 31, 2014, which claims the benefit of European patent Application Number 13174328.8 filed Jun. 28, 2013, which is incorporated herein by reference.

FIELD OF THE INVENTION

The invention relates to an image processing method, to an image processing apparatus, to a mammography imaging system, to a computer program element, and to a computer readable medium.

BACKGROUND OF THE INVENTION

In X-ray tomosynthesis, multiple X-ray projections (for instance, mammograms) from different angles are acquired and computationally combined into a 3D tomographic image volume.

Typically, at least one conventional 2D mammogram is also acquired as a reference image. However, this comes at the expense of yet another radiation dosage exposure. Another option is to use a computational method to generate a "synthetic" mammogram view from the available 3D tomographic image volume.

A method to compute synthetic mammograms is based on the maximum-intensity-projection (MIP) approach and is described in U.S. Pat. No. 7,760,924.

SUMMARY OF THE INVENTION

There may therefore be a need for an alternative method and related apparatus to compute a projection image.

The object of the present invention is solved by the subject matter of the independent claims where further embodiments are incorporated in the dependent claims. It should be noted that the following described aspect of the invention equally apply to the image processing apparatus, to the mammography image processing system, to the computer program element and to the computer readable medium.

According to a first aspect of the invention there is provided an image processing method of forming an (N−k, k≥1)-dimensional projection image in an (N−k, k≥1)-dimensional projection hyperplane (or subspace), comprising:

receiving an N-dimensional image volume made up of image elements, and a definition of at least one spatial projection direction across said volume;

for at least a first and a second image element in a (at least one) hyperplane (or subspace) normal (or orthogonal) to said spatial direction, computing a weight for a plurality of elements; wherein the weight of the first image element is higher than that of the second image element, the weights furnishing a measure for the respective image information content at the at least two image elements;

applying a weighted projecting operation across the N-dimensional image volume and along said spatial direction, thereby projecting at least the first and the second image elements onto respective ones of projection image elements in the projection hyperplane, wherein said weights are applied in the weighted projection operation for each respective element.

In one embodiment, N=3, k=1 and, in particular, according to one embodiment, the image volume is a 3D tomosynthesis volume with the slices forming the various 2D hyperplanes and the projection image to be formed (synthesized) is a synthetic mammogram.

According to the proposed method, the image element with the lower weight assigned is still used in the respective projection operation. This allows the projection image to account for instance to different distributions of image element values within the various hyperplanes in the volume.

In yet other words, a lower weight of, say, the second image element (from the same hyperplane) is still applied in the weighted projection operation and it is not only a higher weight of, say, the first image element that is applied in the weighted projection operation. The weights are not assigned per hyperplane but are assigned to individual image elements within the hyperplanes and each image element from the hyperplane is used in the projection operation where the image element values contribute according to their respective weight. The values of lesser weight image elements (eg, voxels) from the same slice (hyperplane) still contribute to the computation of the value of the respective projection voxel in the projection hyperplane. It is not only the value of the higher weight voxel (from that slice) that contributes to form the projection image.

In this manner the proposed method allows preserving structural details in the image no matter the actual image value (for instance, "brightness" or intensity). Features which are spatially of small extent or have low attenuation (with their voxels having lower brightness) are still accounted for in the synthesized projection image. Spatial resolution can be preserved along with the "sharpness" of the image information in the image volume. Also, optical occlusion (in the projection image) of some structures (e.g. lesions in mammography context) that are visible in the tomosynthesis volume can be prevented. Occlusion may otherwise occur if the structures happen to be situated (in the projection direction) "behind" other, brighter, image elements. As proposed herein, the weights measure and vary with information content, that is, the higher the information content of an image element, the higher the weight. By "information content" as used herein is meant the image structure or image feature that is represented by this image element or its immediate neighborhood (for instance, in voxel terms, the neighborhood diameter is a few (for instance, 5-10) voxels across). There is high information content at an image element if there is high variability between the value of said image element value and that of neighboring image elements in the neighborhood.

According to one embodiment the computation of the weights comprises the computation of a magnitude of a gradient of the at least two image elements or of image elements in the respective neighborhoods of the two image elements.

According to one embodiment the gradient magnitude measurement includes establishing an edge measure. More particularly, and according to one embodiment, the gradient magnitude measurement includes the step of applying a Sobel filter but other filter that are capable of responding to image structure information such as the Canny edge operator are also envisaged. In an alternative or supplementary embodiment, the computation of weights includes a CAD (computer aided design) image feature detection in respective neighborhoods of the at least two image elements.

According to one embodiment the weight computation is i) carried out across substantially the whole image volume T before commencement of the weighted projection operation or ii) is carried across only a part of the image volume T before commencement of the weighted projecting operation. According to one embodiment the weight computation is carried out as the weighted projecting operation proceeds across the volume T in said direction. The adjustability of volume and time in these embodiments, allows adapting the proposed method to existing work flows (eg, scheduling requirements) and/or memory/CPU time constraints.

According to one embodiment the weighted projecting operation includes a forward-projection across the volume T but other projection methods (for instance, including a temporal component as in the next embodiment) are also envisaged herein.

According to one embodiment the image volume is a dynamic "4D" volume (N=4, k=2) and wherein the weight computation step includes computing both, a temporal and a spatial gradient component, and the projection hyperplane corresponds to a dynamic 2D projection view.

According to one embodiment the image elements are individual voxels or are elements of a coarser partition of the volume. In one embodiment, the size of the image elements can be adjusted thereby providing a means to strike a useful balance between resolution requirements and computation time and/or memory constraints.

The main application of the proposed method (but by no way restricted thereto) is screening and diagnosis in X-ray mammography. With the present approach, the conventional 2D mammograms (that is, an actual image acquisition (non-synthesized) on top of those involved for the previously acquired tomosynthesis volume block) may be omitted and the synthesized image may replace conventional 2D mammograms. Any kind of tomosynthesis application such as lung/chest tomosynthesis, orthopedics tomosynthesis will benefit from this method. The method can also be applied to other imaging modalities which provide 3D volumes for instance, breast CT, chest CT, chest MR, and others.

Also, the projection used by the forward-projector may be a parallel or a central projection or other.

Also, application of the proposed method to higher dimensional data sets (N≥4) is also envisaged with projection on hyperplanes or (subspaces) with dimensions (n≥3) for instance in data mining operations or data volumes acquired in geological or astronomical measurements and others.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
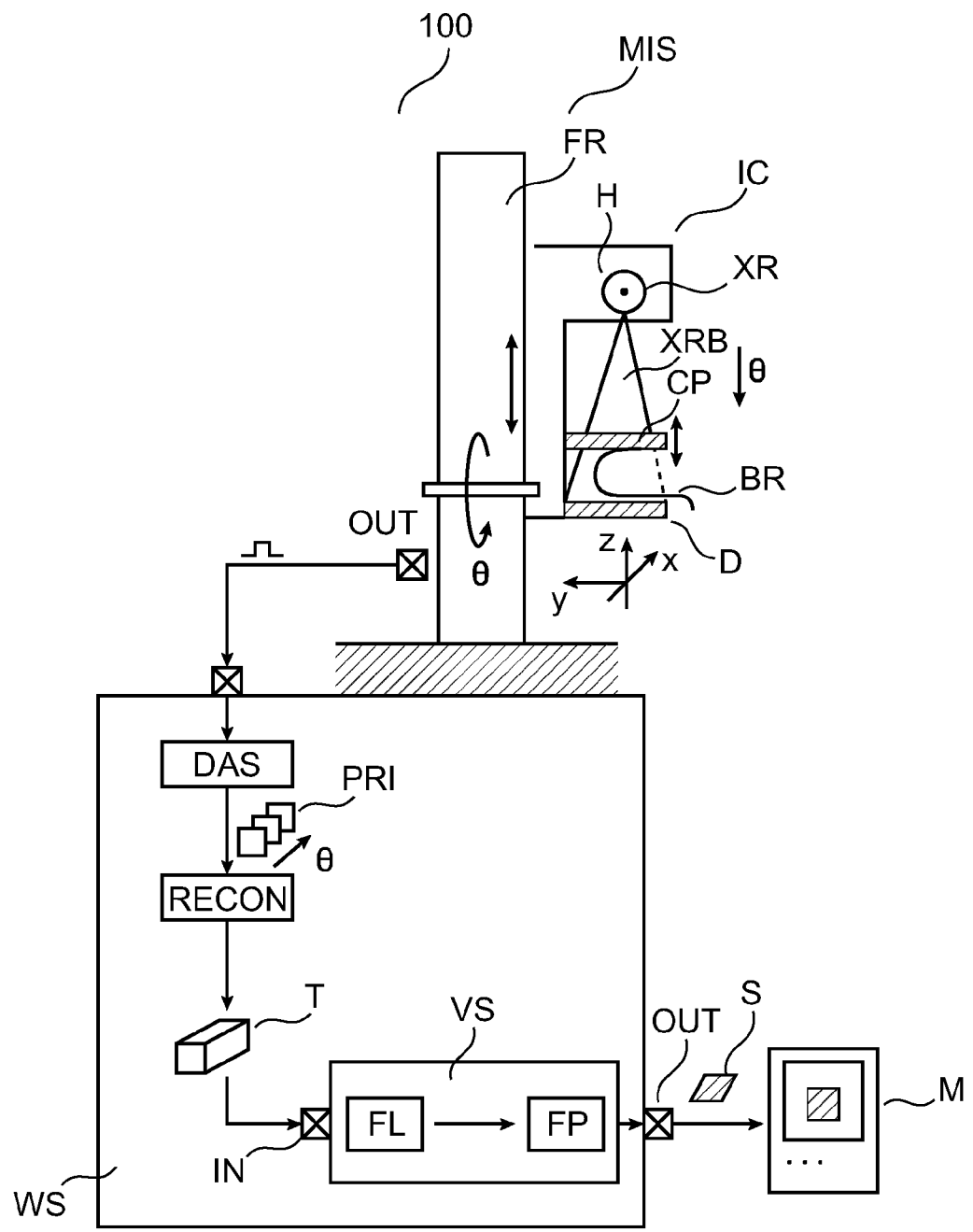
FIG. 1 shows a block diagram of an imaging arrangement including a view synthesizer.

With reference to FIG. 1, there is shown an imaging arrangement 100 according to one embodiment. The arrangement 100 comprises a mammography imaging system MIS and a workstation WS for controlling operation of said mammography imaging systems MIS.

Mammography imaging system MIS includes a frame FR which is either wall mounted or freestanding. On said frame FR, a rigid imager carriage IC is mounted so as to be slidable along a vertical axis y. The imager carriage is energizable by a suitable actuator-controller arrangement for precise positioning along said axis to so accommodate the imaging system to height requirements of a patient whose breast BR is to be imaged.

The imager carriage IC is generally elongate and carries on one end an X-ray source XR and on the other end an X-ray radiation sensitive detector D. The carriage IC is housed in a housing H having a cut-out which defines an examination region between X-ray source XR and detector D. In other words, detector D is located opposite the radiation source XR, across the examination region to receive the radiation beam XBR after its passage through a region of interest ROI. In the examination region, there is slidably (along vertical z-axis) arranged a compression plate CP that can be shuttled between X-ray source XR and detector D either manually or by energizing same via a suitable actuator-controller arrangement. The imager carriage IC is also rotatable around vertical y axis with said y axis passing through the examination region and orthogonal to z axis. Rotation is effected upon energizing the carriage via a suitable actuator controller arrangement, whereupon the X-ray source and hence the detector travel in a generally circular orbit around the examination region. In this manner, X-ray source (and hence detector D) can assume a range of desired angular positions relative to the examination region. Each angular position θ of the carriage IC defines an imaging or projection direction (likewise referred to hereinafter as θ) as will be explained in more detail below. Simpler embodiments may also allow effecting rotation manually in which case suitably positioned handle options are arranged on housing H.

The imaging system MIS is connected via suitable interfaces means OUT and across a communication network to a workstation WS. In general, workstation is a computing system with which a clinician ("user") is able to control operation of the imaging system. According to one embodiment, there is also a display unit or monitor M which is controlled by work station WS and which allows displaying of images that are acquired by the imaging system. Workstation WS runs an operating system which in turn controls execution of a number of modules whose operation will be explained in more detail below.

In use, the carriage IC receives a control signal from work station WS and is thereby instructed to rotate into a desired angular position θ relative to the examination region and the carriage moves into a height appropriate z-position. Patient is then asked to introduce the relevant breast BR into the examination region. Compression plate CP then slides downwardly and into contact with breast BR to gently compress breast BR against a breast support (not shown in FIG. 1) arranged between plate CP and detector D to ensure image quality. Compression plate CP and breast support are so arranged that carriage IC can rotate about same whilst both, plate CP and breast support, remain stationary. X-ray source XR is then energized to emit an X-ray beam XRB that passes through the breast tissue at projection direction θ. In its passage through the breast tissue said X-ray beam XRB experiences attenuation at different levels. Attenuation levels are a function of the density distribution in the breast tissue. It is the so attenuated X-ray beam XRB that is then incident on the detector D's image plane. Detector D's image plane is made up of a number of individual detector cells that are arranged in one or more rows and columns to form an array. Each cell responds to an individual radiation ray of beam PRX. Specifically, the response at each cell is in the form of an electrical signal that varies directly with the intensity (or energy flux) of (or in) the ray.

Projection "raw data" as supplied by the detector D is processed by a DAS (data acquisition system) to form an (acquired) projection image PRI of the ROI along a current view θ. Specifically, the collection of said raw data signals are translated by DAS into a respective digital (pixel) values representative of the accumulative density across the breast BR in the instant projection direction θ.

For tomosynthesis imaging, whilst breast BR remains compressed between plate CP and breast support, the imager carriage IC (and with it X-ray source XR) then rotates by a certain angular increment Δθ and the above measurements are repeated. In his manner, a set of projection data from different projection directions $\theta_i$ is obtained. As such, the outlined imaging procedure is very similar to CT (indeed, in one embodiment the imager may very well be a CT or other imagers, as the MIS shown in FIG. 1 is but one exemplary embodiment), but in a mammography the projection directions are not across the full circle but are limited to an arc segment. Typically, there are only two main directions $\theta_{CC}$ for a caudocranial (CC) view and $\theta_{MLO}$ for a mediolateral oblique (MLO) (at 12 o'clock and approximately 2 o'clock considered in frontal view along y axis in FIG. 1), with respective arc segments $\theta_{CC}-\Delta\theta \leq \theta_i \leq \theta_{CC}+\Delta\theta$ and $\theta_{MLO}-\Delta\theta \leq \theta_j \leq \theta M_{LO}+\Delta\theta$ centered around each of the two main views. The breast support does not rotate whilst carriage IC (and X-ray tube XR in particular) sweep out the respective arc segments $\theta_j$, about the respective main directions CC, MLO but does move when the carriage IC changes over from one main direction (CC or MLO) to the other (MLO or CC).

The imager system 100 includes a tomosynthesis reconstructor RECON which is capable to reconstruct from the projection images associated with said θ value, a slice image SL for each z, despite the relatively few number very limited angular projections $\theta_i$. "Reconstruction" means solving for the tissue densities μ in the respective x,y plane (for each z). To this end, in tomosynthesis, a special variant of the familiar CT filtered back-projection (FBP) algorithm or similar may be used by the reconstructor RECON. In each slice, the reconstructed values represent the pointwise density/attenuation level of the imaged breast BR tissue. The values in each slice are mapped onto suitable gray or color scale of a palette. The mapped values can then be forwarded to a renderer that interacts with a video card to drive monitor M where the slice images may then be displayed. The slice images SL may also be stored in a database DB or otherwise post-processed. Each slice when rendered for display provides to the user a cross-sectional view on the internals of the breast at the z-position so that diagnostically relevant structures such as micro-calcifications or tissue abnormalities can be identified. The collection of slices $SL_j$ together form a volumetric image data set T indicative of the examination region. The volume is made up of a number of discrete image elements, or voxels, each having a position (x,y,z) and each carrying a numerical value ("voxel value") that encodes the reconstructed density/attenuation level.

On occasion the user may be desirous to have a projection view or image ("mammogram") of the complete breast BR similar to a conventional 2D mammogram which summarizes or consolidates the image information of the T tomosynthesis block into a single 2D image to help the user navigating the T volume which is more difficult and time-consuming than in a lower, 2D space. In other words, a 2D projection image can serve as an "overview" image on the T tomosynthesis block that may include highly involved structures. Note that the 2D raw projection views are usually not suited to this purpose as they are usually acquired with much lower X-ray dose than a conventional 2D mammogram and hence exhibit significantly higher noise than a conventional 2D mammogram or the reconstructed 3D volume.

To address this need, the arrangement as proposed herein includes a view synthesizer VS that allows to computationally synthesize the desired 2D projection view S from the available T tomosynthesis block. There is therefore no need to operate the imager MIS to actually acquire a further 2D mammogram. A consequential, further radiation exposure of the patient can be avoided.

The view synthesizer VS includes an input port IN, a filter module FL, a forward projector FP and an output port OUT. Briefly, the view synthesizer VS receives block T (or a storage/memory reference thereto) and a desired view or projection direction p. Filter module FL and forward projector FP then operate on said block T, in a manner to be described in more detail below, to produce the desired synthetic mammogram S which is then output at output port OUT. Synthetic mammogram S can then be rendered for display on monitor M.

Figure 2:
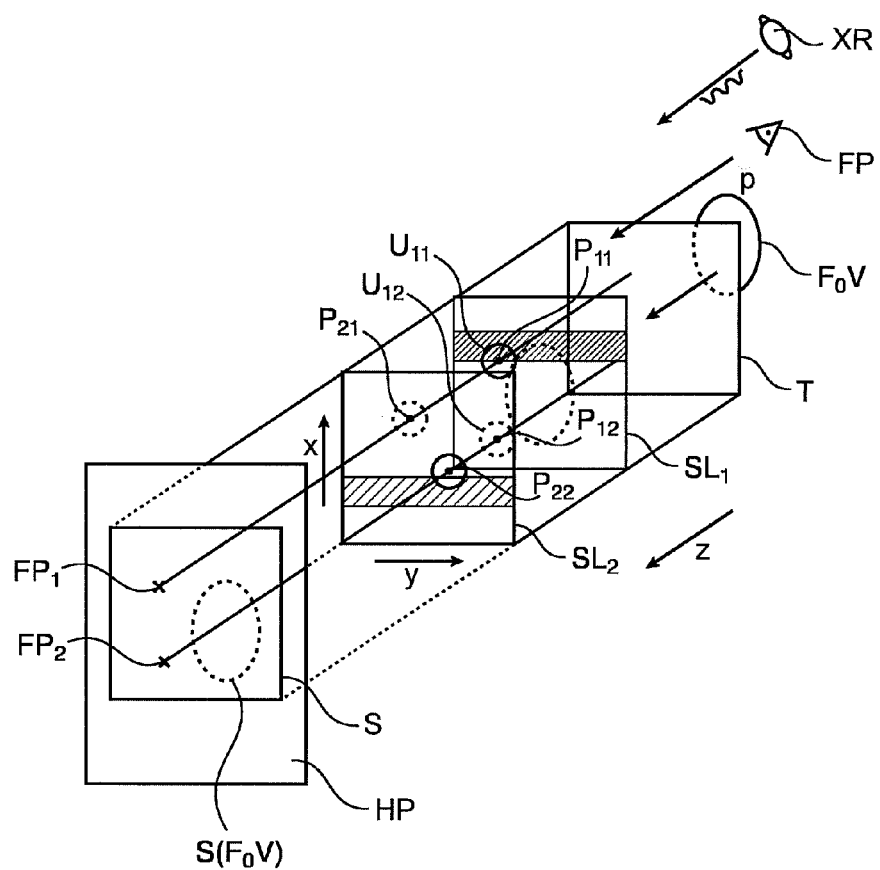
FIG. 2 shows operation of the view synthesizer of FIG. 1 on a 3D image volume.

Reference is now made to FIG. 2, which shows a simplified representation of the 3D volume T on which view synthesizer VS acts. Only two slice images SL1,2 (ie, in this embodiment, 2D hyperplanes) are shown for explanatory purposes with the understanding that the 3-D volume is usually made up of several tens of such slices. Likewise, again for explicative purposes, only two voxels per slice are shown, that is voxels P11, P12 in slice SL1 and voxels P21, P22 in slice SL2. In the example of FIG. 2, synthetic mammogram S is computed for projection direction p which happens to be parallel to the z-axis. When projecting along the z-axis, the computations involved turn out particularly simple because no interpolation is required as would be the case for other directions p not parallel to z-axis. Other projection directions p are also envisaged, for example in contexts where the volume has no preferred direction, such as isotropic magnetic-resonance images (MRI).

The requested projection direction p defines a projection hyper plane HP, in this simple case defines a 2D plane, onto which the desired synthesized mammogram S is to be (mathematically) projected. To this end, a family of (mathematical) lines that run parallel to the requested projection direction p) are cast across the volume T. Each line "picks up" the values of the voxels it passes though and carries same to the respective projection point FP1, FP2, where the respective lines intersect projection plane HP. It is proposed herein, that projection points FP1, FP2 are not simply computed by summing over the picked up voxel values, but voxels with higher information content (for instance a high edge measure) are emphasized or given more weight in the synthetic image S. This allows better accounting for the high anisotropy of the point spread function (PSF) in tomosynthesis images. Due to this effect, most structures are sharply represented in only one or two slices of the volume but quickly blur or fade when moving towards the adjacent slices.

View synthesizer VS operates in one embodiment to generate synthetic mammogram S based on an edge measure or similar instead of using a simple averaging or MIP-like approaches. This is shown schematically in FIG. 3. In each slice image SL1, SL2, a region that carries high structural information (content) are represented as hachured bars. In slice SL1, voxel P11 is an edge point and carries therefore more structural information than point P12 which happens to be situated in a more homogeneous portion of slice SL1. In slice SL2, the structurally more interesting part is situated at the bottom portion of said slice with point P22 being an edge point whereas point P21 is not. Therefore, forward projector FP will operate to attach higher weight to edge point P11's value (in slice SL1) when forming the projection point FP1 than the smaller weight to non-edge point P12 of the same slice SL1 when forming the other projection point FP2. In other words, it is proposed to calculate the forward projections using a weighted average function along the projection direction p (in this case, z-direction). The weighting function is set up so that regions within slice(s) with maximum sharpness or "edginess" (or sharpness/edginess higher than a user definable threshold) are assigned highest weight within the respective slice or even across all slices. This, that is, the voxel-wise weighting across, in one embodiment, all slices SL1, SL2, can be achieved for example by applying a filter algorithm to the reconstructed volume T that generates a high response at strong edges, from which the weighting function can be derived in a normalization step. This ensures that sharp structures and edges in the tomosynthesis volume T are retained or preserved, substantially without blurring because by averaging with irrelevant slices or hiding it behind other, brighter structures. In other words, and very much unlike previous simple averaging or MIP approaches, it is not simply the "brightest (most intense)" voxel that prevails in the computation of the projection, but it is the voxel that carries the most information content that attracts the highest weight. In particular, it matters whether the voxel is an edge point, which may in fact be a point with rather low intensity. In yet other words, it is the presence of edges in the immediate, user-adjustable neighborhood U11U12 of said low intensity point that determines whether said voxel carries high information content rather than the magnitude of voxel ("face") value in and of itself. Again, in one embodiment, it is not required that a point be located exactly on an edge for it to be assigned a high weight. Instead, the presence of edges in its neighborhood U11, U12 is a sufficient criterion in some embodiment.

The synthetic mammogram S is computed in accord with the proposed method from a 3D weighted average of the reconstructed 3D volume T by applying a weighted projection to the 3D weighted volume T. This can be formally summarized in the following equation:

$$\frac{FP(w(r) \cdot T(r))}{FP(w(r))} \quad (1)$$

with i) the 3D-Voxel position r in volume T, ii) the spatially adaptive 3D weight function w(r), which ensures that structures of interest remain sharp and are not blurred when forward-projected with the forward projection operator FP(.). The weighting as proposed herein is 3D or "fully spatially" adapted in the sense that the weight function not merely attaches weights per slice (or, in general, per hyperplane) but the weights are assigned across substantially all dimensions (in particular to in-plane voxels making up each of the slices themselves) of the 3D block through which the forward-projector is to project across.

In one embodiment, there is also a normalization (that is multiplication by 1/FP(w(r)) ensures that the relative relationship between the voxel values on each projection line is preserved. The normalization respects, that is, preserves, the relative magnitudes along each projection line. Normalization is separately for each projection line and the normalized weights add up to unity along each projection line.

Operation

Figure 3:
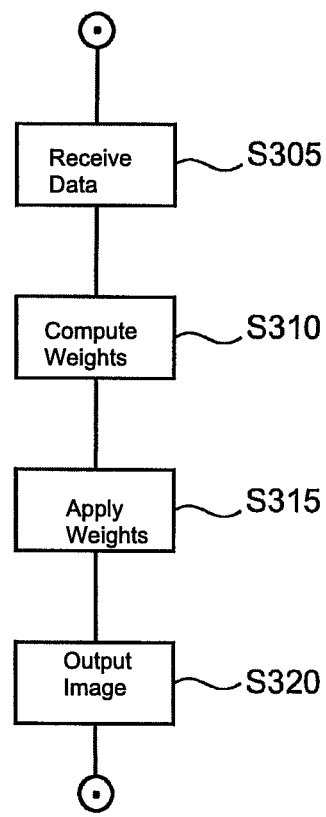
FIG. 3 shows a flow chart of an image processing method.

Operation of view synthesizer VS will now be explained in more detail with reference to flowchart of FIG. 3.

At step S305, a specification of the relevant 3D volume T and the desired projection direction p for the synthesized projection image (for instance, a mammogram) S is received.

At step S310 the weights w for the voxel elements P11, P12, P21, P22 are computed.

In one embodiment this is implemented as follows: Let e(r) be a suitable edge measure, defined for every voxel position r within the 3D tomosynthesis volume T(r). Such an edge measure can be obtained, for instance, by applying the Sobel operator (or a Canny edge detector or similar) filter. The response is "proportional" to (or at least varies directly with) the information content one wishes to quantify in the volume T. Let then w(r)=f[e(r)] be the local weights, where f is a function for "shaping" the weights, in other words, the actual filter responses are mapped onto a suitable scale so they can be used as weights in the desired form). For instance, one may wish to have only positive numbers as weights or the weights are to lie in the unit interval, and so on. According to one embodiment, weight shaper f is the identity function so the filter responses themselves are used as weights but whether or not this is possible depends on the numerical range of the filter module FL.

In step S315, forward projector FP operates to apply a weighted projection operation to the so weighted volume T. With reference to FIG. 2, the value of each projection point, for instance FP1 is a function of the values of those volume voxels P11, P21 that are projected onto said projection point. The weight of each volume voxel then determines the relative "contribution" of said volume voxel value in the computation of the value of the projection point FP1. The synthetic mammogram S can then be computed as the weighted projection according to Equation (1). According to one embodiment, the forward projection will operate along either one of the two main directions CC, MLO. In other words, the forward projection will operate orthogonally through the tomosynthesis slices to avoid interpolation. It is then reasonable to use a geometry-matched grid or coordinate system for the previous volume reconstruction such that the tomosynthesis-artifacts are aligned with the grid. This amounts to effectively re-scaling each of the slices such that the magnification effect of the X-ray cone beam is compensated.

In such a case, equation (1) can be written as $$S(x, y) = \sum_{z=0}^{N} w'(x, y, z) \cdot T(x, y, z) \quad (2)$$

where x and y are the in-plane coordinates per slice SL, z is the through-plane coordinate (usually in the direction of the X-rays) and N indicates the number of reconstructed slices in the tomosynthesis volume. Furthermore, w' denotes the normalized spatially adaptive weight function w'(x,y,z)=f[e(x,y,z)]. The weights are normalized such that the mean attenuation value (as encoded in the voxel values) is retained along the through-plane coordinate z. One method to transform into said geometry matched grid is described in U.S. Pat. No. 7,702,142.

The proposed method retains edges (or other structures of interest) which would turn out less sharp in the MIP or similar "winner takes is all" approaches.

Use of any kind of image feature/structure enhancement filter is envisaged herein instead of the Sobel-filter mentioned above which is merely an exemplary embodiment. In this way it is possible to enhance certain features in the tomosynthesis volume prior to the forward projection step as per step S315 for the computation of the synthetic mammogram via Equation (1).

Moreover, and as explained in more detail below, the proposed method can also be combined with CAD-based techniques to obtain the spatially adaptive weighting function w'(x,y,z)=f[e(x,y,z)], which are optimized to enhance edges, lesion, vessels, calcifications or spiculated masses with a suitable CAD-algorithm.

In step S320, synthesized projection image S is output via output port OUT. The projection image S may then be rendered for view on display unit M or stored in a database or otherwise image-processed.

As mentioned earlier, the Sobel operator is but one embodiment for the filter module FL to define an edge measure. Other embodiments are spatial gradient computations where a high gradient magnitude is taken to indicate volume portions of high information or structural content. In yet other embodiments, filter module FL includes a CAD (computer aided design) image feature detector. In CAD, operation is based on a library of features or templates such as different shapes of different sizes for different types of lesions, degrees of calcifications or, in other than mammography contexts, on shape footprints of certain organs of interest such as vessels or brain structures, etc. The CAD detector scans the volume T and detects those voxels that match said shape templates. The matched voxels may constitute suspicious shapes that are indicative to lesions spiculated masses etc. Measured against a user definable level of confidence, it is then decided whether or not a given voxel does form part of such a suspicious shape structure. Depending on the level of confidence of a given voxel, the weight is assigned accordingly: a high confidence will attract a higher weight whereas a low confidence a correspondingly lower weight.

Some of the filter modules FL embodiments (such as the Sobel operator or the CAD detector) operate on voxel neighborhoods U11, U12. According to one embodiment, the neighborhood sizes (for instance measured in voxel units across) are adjustable by user interaction. For instance in one embodiment, a graphical user interface is envisaged that allows the user to adjust neighborhood size on which filter module FL is to operate. Text based input means are likewise envisaged in some embodiments. Adjusting the voxel neighborhood U11,U12, size adds a degree of flexibility when interfacing with different filter modules each requiring different neighborhood sizes. In this embodiment, at step S305, a specification of a size of at least one of the neighborhoods (U11, U12) is received and the neighborhood is re-sized accordingly.

Although in a preferred embodiment, filter module FL acts to assign information content weight substantially to all voxels in the volume, there are embodiments envisaged where this is not the case. For instance in one embodiment the user can specify a sub-volume along which the forward projection is to be taken. This volume restriction would allow saving CPU time. In this embodiment, it is envisaged that the user specifies for, instance by touch screen or pointer tool action in a graphical user interface on which the 3D volume T is displayed, a "projection window" (or field of view FoV), or a subset of slices S(FoV) for projection purposes. This is indicated in FIG. 2 by the dashed circle but the projection window FoV may take any desired shape such as a square or rectangular. The projection lines are then cast only across the so specified sub volume.

According to yet another embodiment, it is also the timing of the weights computation by filter FL that is adjustable. In one embodiment, the voxel weights are computed prior commencement of the forward projection by for projector FP. In yet another embodiment, the weights computations are executed in parallel with the computation of the forward projection summation as per equation (2). The respective weights are computed summand-wise as the summation along the respective lines per equation (2) unfolds.

According to yet another embodiment in order to save CPU time, the view synthesizer VS affords to the user a functionality of "coarsening" the 3-D volume by using an under-sampling algorithm: adjacent voxels are collapsed into new, coarser image elements into which volume T is partitioned. In other words, the 3-D volume is shrunk down in size so that the summation in equation (2) will extend across fewer terms and fewer weights will need to be computed.

In one embodiment the computation of the gradient at each voxel includes a temporal gradient component as well. This is of particular relevance when a projection image is to be synthesized (N=4, k=2) for a dynamic 3-D volume, that is, for a times series of 3D volumes, also referred to as a 4D image volume. Because of the temporal gradient, image portions that vary strongly with time across the different 3D volumes will attract a high weight. In this embodiment, the projection hyperplane (HP) corresponds to a dynamic 2D projection view that allows the user to view the evolution, that is, changes over time of structures across the 3D volumes in a projection view along the desired direction p.

The components of view synthesizer VS, that is, filter module FL and forward projector, may be programmed in a suitable scientific computing platform such as MATLAB® and then translated into C++ or C routines maintained in a library and linked when called on by work station WS. MATLAB® for instance, features an "IMAGE PROCESSING TOOLBOX®" with a SOBEL operator module. The components may be arranged as dedicated FPGAs or as hardwired standalone chips.

Figure 4A:
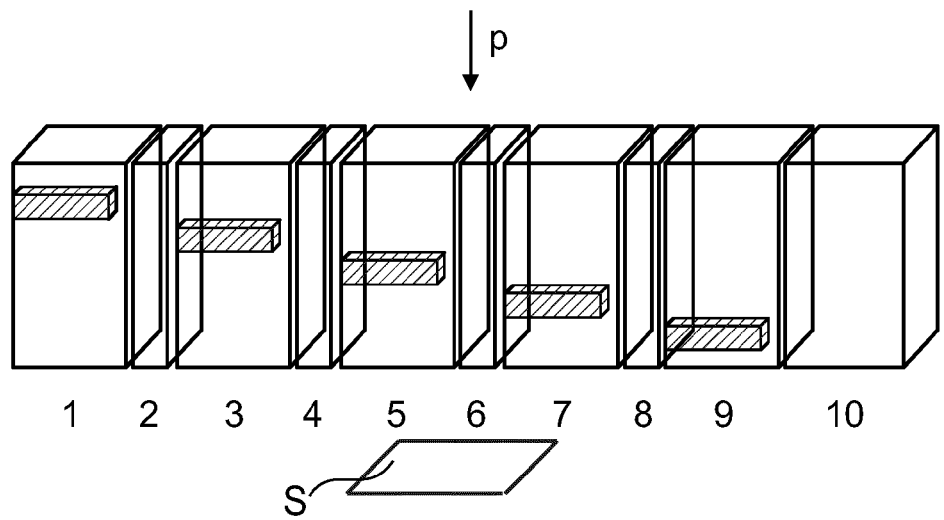
FIG. 4 shows operation of the method of FIG. 3 on various phantoms.

Referring now to FIG. 4A,B, there is shown the effect of the proposed method of projection image synthesizing when applying same to certain phantom bodies and how the synthesized images differ from other approaches.

The method for generating synthetic mammograms as proposed herein allows preserving essentially the full spatial resolution of the tomosynthesis volume for structures of interest (e.g. fine micro-calcifications).

The phantom in FIG. 4A comprises several blocks (numbered 1-10) of phantom tissue. A first type of these blocks (odd numbered) contains only one structure (shown as horizontal bars in dark hachure) of relatively dense material, located at a certain height, each embedded in a homogeneous background of lesser density. For the surrounding material, an adipose- and glandular-equivalent material can be used as supplied for instance by medical phantom maker CIRS Inc. of Norfolk, Virginia, US. The respective height of the structured bars is different in each of the odd-numbered phantom blocks to allow sampling a range of depth locations.

Another set of homogeneous blocks (even numbered) is manufactured such that the overall density of these blocks is equal to the average density of each of the structured blocks (the odd-numbered ones), e.g., a parallel X-ray projection would return the same attenuation image for each of the blocks 1-10.

In other words, with this phantom, a simple averaging function will produce a uniform synthetic mammogram, and a slice-weighted average function will highlight, in the synthetic mammogram, only one of the dark bars from the odd numbered blocks, namely the one located in the slice which receives the highest weight. In contrast, the proposed method returns synthetic mammograms where each of the dark bars (or at least its lateral edges and the surrounding neighborhood) would be represented ("visible"). This is because of the spatially adapted weighting function FL that assigns weights to voxels "in-plane" per slice, and the forward projector FP then projects not only a single voxel (the one with maximum weight) on the projection hyperplane, but all voxels values from said plane weighted according to their weights. In other words, the proposed method will not merely produce a homogeneous projection, but will respond instead to the variations of density distributions in the blocks 1-10. Therefore, the phantom in FIG. 4A allows discriminating a synthetic mammogram that is computed from a (weighted) average computation where the weights are merely assigned per slice from a synthetic mammogram as computed according to the method proposed herein.

Figure 4B:
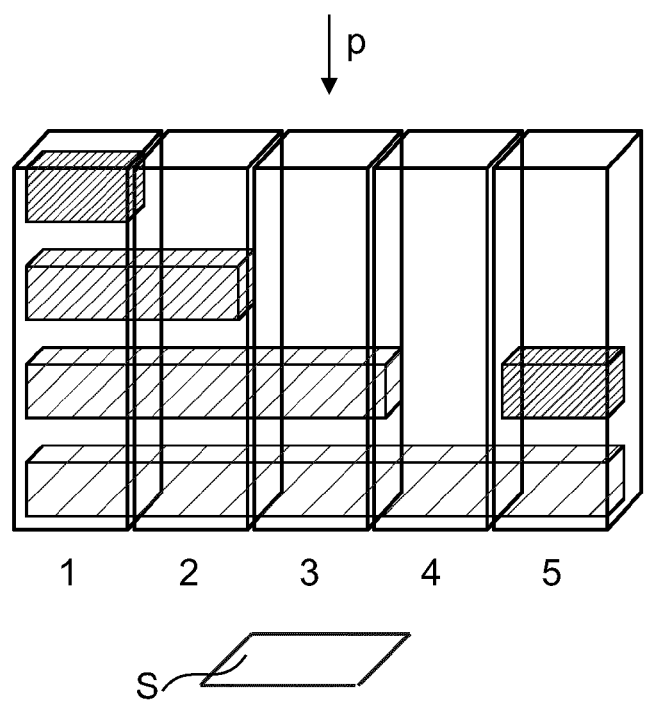

In FIG. 4B, a second test phantom is shown. A series of blocks with increasing density (shown with increasing heaviness of the hachures from top to bottom) but decreasing length is stacked on top of each other and aligned to the left. An additional block with highest density and smallest length is aligned to the right on top of the lowest block. With this phantom, a Maximum-Intensity-Projection will produce a decreasing signal from column 1 to 4 in the synthetic mammogram, expect for column 5 which will have the same signal as that returned for column 1. The proposed algorithm will in contrast produce a different signal in the synthetic mammogram for each of columns 1-5, because of the differently pronounced edges in each bar. In other words, this phantom can be used to discriminate between an MIP algorithm and the method as proposed herein.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A mammography imaging system including at least one computer processor programmed to perform a computer-implemented tomographic image processing method of forming an (N−k, k≥1 and k=N−2, where N=3 or 4)-dimensional projection image in an (N−k)-dimensional projection hyperplane or subspace, the method comprising:

receiving i) an N-dimensional image tomographic volume made up of image elements comprising individual voxels acquired by an imaging system, and ii) at least one spatial projection direction across said volume to the (N−k) dimensional projection hyperplane;

form a projection image from the received tomographic volume and the at least one spatial direction:

for at least a first and a second image element (N−k)-projection hyperplane or subspace normal to said spatial direction, computing a weight for a plurality of elements according to $w(r)=f[(e(r)]$ where f is a function to determine a shape of the weights, and e(r) is an edge measure for a voxel r; wherein the weight of the first image element is higher than that of the second image element, the weights furnishing a measure for respective image information content at the at least two image elements;

applying a weighted projecting operation across the N-dimensional image volume and along said spatial direction according to $S(x, y)=\Sigma_{z=0}^{N} w'(x,y,z)*T(x,y,z)$ where x and y are in-plane coordinates for an image slice of the tomographic volume, z is a through-plane coordinate of the image slice, N is a number of reconstructed slices in the tomographic volume, w' is a weighting function, and T is the tomographic volume, thereby projecting at least the first and the second image elements onto corresponding projection image elements in the projection hyperplane, wherein said weights are applied in the weighted projection operation for each respective element, wherein the weighted projecting operation includes a forward-projection across the volume.

2. The mammography imaging system of claim 1, wherein the computation of the weights comprises the computation of a magnitude of a gradient at the at least two image elements or of image elements in the respective neighborhoods comprising 5-10 voxels inclusive of said at least two image elements.

3. The mammography imaging system of claim 1, wherein the gradient magnitude measurement includes establishing an edge measure.

4. The mammography imaging system of claim 3, wherein the gradient magnitude measurement includes applying a Sobel filter.

5. The mammography imaging system of claim 1, wherein the computation of weights includes a computer-aided-design image feature detector, which performs template matching in respective neighborhoods of the at least two image elements to determine the weights.

6. The mammography imaging system of claim 1, wherein the weight computation is carried out across the whole image volume before commencement of the weighted projection operation.

7. The mammography imaging system of claim 1 wherein the weight computation is carried out as the weighted projecting operation proceeds across the volume in said direction.

8. The mammography imaging system of claim 1, wherein the image volume is a tomosynthesis volume and the projection image is a synthetic mammogram.

9. The mammography imaging system of claim 1, wherein the image volume is a dynamic 4D volume and wherein the weight computation includes computing both, a temporal and a spatial gradient component, and the projection hyperplane corresponds to a dynamic 2D projection view.

10. A non-transitory computer readable medium, which, when being executed by a processing unit, is adapted to perform a computer-implemented tomographic image processing method of forming an (N−k, k≥1 and k=N−2, where N=3 or 4)-dimensional projection image in an (N−k)-dimensional projection hyperplane or subspace, the method comprising:

receiving i) an N-dimensional image tomographic volume made up of image elements comprising individual voxels acquired by an imaging system, and ii) at least one spatial projection direction across said volume to the (N−k) dimensional projection hyperplane;

form a projection image from the received tomographic volume and the at least one spatial direction;

for at least a first and a second image element in an (N−k)-projection hyperplane or subspace normal to said spatial direction, computing a weight for a plurality of elements according to $w(r)=f[(e(r)]$ where f is a function to determine a shape of the weights, and e(r) is an edge measure for a voxel r; wherein the weight of the first image element is higher than that of the second image element, the weights furnishing a measure for the respective image information content at the at least two image elements;

applying a weighted projecting operation across the N-dimensional image volume and along said spatial direction according to $S(x, y)=\Sigma_{z=0}^{N}w'(x, y, z)*T(x, y, z)$ where x and y are in-plane coordinates for an image slice of the tomographic volume, z is a through-plane coordinate of the image slice, N is a number of reconstructed slices in the tomographic volume, w' is a weighting function, and T is the tomographic volume, thereby projecting at least the first and the second image elements onto respective ones of projection image elements in the projection hyperplane, wherein said weights are applied in the weighted projection operation for each corresponding element, wherein the weighted projection operation includes a forward-projection across the volume.

11. The non-transitory computer readable medium of claim 10, wherein the computation of the weights comprises the computation of a magnitude of a gradient at the at least two image elements or of image elements in the respective neighborhoods comprising 5-10 voxels inclusive of said at least two image elements.

12. The mammography imaging system of claim 10, wherein the gradient magnitude measurement includes establishing an edge measure.

13. The non-transitory computer readable medium of claim 12, wherein the gradient magnitude measurement includes applying a Sobel filter.

14. The non-transitory computer readable medium of claim 10, wherein the computation of weights includes a computer-aided-design image feature detector, which performs template matching in respective neighborhoods of the at least two image elements to determine the weights.

15. The non-transitory computer readable medium of claim 10, wherein the weight computation is carried out across the whole image volume before commencement of the weighted projection operation.

16. The non-transitory computer readable medium of claim 10, wherein the weight computation is carried out as the weighted projecting operation proceeds across the volume in said direction.

17. The non-transitory computer readable medium of claim 10, wherein the image volume is a tomosynthesis volume and the projection image is a synthetic mammogram.

18. The non-transitory computer readable medium of claim 10, wherein the image volume is a dynamic 4D volume and wherein the weight computation includes computing both, a temporal and a spatial gradient component, and the projection hyperplane corresponds to a dynamic 2D projection view.

19. A mammography imaging system including at least one computer processor programmed to perform a computer-implemented tomographic image processing method of forming an (N−k, k≥1 and k=N−2, where N=3 or 4)-dimensional projection image in an (N−-k)-dimensional projection hyperplane or subspace, the method comprising:

receiving i) an N-dimensional image tomographic volume made up of image elements comprising individual voxels acquired by an imaging system, and ii) at least one spatial projection direction across said volume to the (N−k) dimensional projection hyperplane;

form a projection image from the received tomographic volume and the at least one spatial direction;

for at least a first and a second image element (N−k)-projection hyperplane or subspace normal to said spatial direction, computing a weight for a plurality of elements according to $w(r)=f[(e(r)]$ where f is a function to determine a shape of the weights, and e(r) is an edge measure for a voxel r; wherein the weight of the first image element is higher than that of the second image element, the weights furnishing a measure for respective image information content at the at least two image elements;

applying a weighted projecting operation across the N-dimensional image volume and along said spatial direction according to $S(x, y)=\Sigma_{z=0}^{N} w'(x, y, z)*T(x, y, z)$ where x and y are in-plane coordinates for an image slice of the tomographic volume, z is a through-plane coordinate of the image slice, N is a number of reconstructed slices in the tomographic volume, w' is a weighting function, and T is the tomographic volume, thereby projecting at least the first and the second image elements onto corresponding projection image elements in the projection hyperplane, wherein said weights are applied in the weighted projection operation for each respective element, wherein the weighted projecting operation includes a forward-projection across the volume;

wherein the computation of the weights comprises the computation of a magnitude of a gradient at the at least two image elements or of image elements in the respective neighborhoods comprising 5-10 voxels inclusive of said at least two image elements; and wherein the gradient magnitude measurement includes establishing an edge measure.

20. The mammography imaging system of claim 19, wherein the image volume is a dynamic 4D volume and wherein the weight computation includes computing both, a temporal and a spatial gradient component, and the projection hyperplane corresponds to a dynamic 2D projection view.

* * * * *